United States Patent [19]
Ghorpade et al.

[11] Patent Number: 5,859,263
[45] Date of Patent: Jan. 12, 1999

[54] METHOD AND APPARATUS FOR PRODUCTION OF LEVULINIC ACID VIA REACTIVE EXTRUSION

[75] Inventors: Viswas M. Ghorpade; Milford A. Hanna, both of Lincoln, Nebr.

[73] Assignee: Board of Regents University of Nebraska Lincoln, Lincoln, Nebr.

[21] Appl. No.: 696,764

[22] Filed: Aug. 14, 1996

Related U.S. Application Data

[60] Provisional application No. 60/018,096 May 22, 1996.
[51] Int. Cl. [6] .................. C07D 307/26; C07C 31/18; C07C 51/00
[52] U.S. Cl. .................. 549/326; 568/853; 585/603; 585/604; 562/515
[58] Field of Search .................. 562/515; 585/603, 585/604; 568/853; 549/326

[56] References Cited

U.S. PATENT DOCUMENTS

| | | | |
|---|---|---|---|
| 2,195,570 | 4/1940 | Hovey et al. | 260/65 |
| 2,206,311 | 7/1940 | Thompson | 260/528 |
| 2,270,328 | 1/1942 | Moyer | 260/528 |
| 2,813,900 | 11/1957 | Dunlop et al. | 260/528 |
| 3,065,263 | 11/1962 | Carlson et al. | 260/528 |
| 3,258,481 | 6/1966 | Sassenrath et al. | 260/528 |
| 4,897,497 | 1/1990 | Fitzpatrick | 549/489 |

OTHER PUBLICATIONS

Ghorpade, et al., "Industrial Applications for Levulinic Acid", pp. 1–7, Industrial Agricultural Product Center, University of Nebraska–Lincoln.

Leonard, "Levulinic Acid as a Basic Chemical Raw Materials", pp. 1331–1341, Industrial and Engineering Chemistry.

Hands, et al., "The Preparation of Levulinic Acid on a Semi–Technical Scale", Nov., 1947, pp. 415–416, J.S.C.I., 66.

Thomas, et al., "Studies on Levulinic Acid. I. Its Preparation from Carbohydrates by Digestion with Hydrochloric Acid Under Pressure", Jun. 8, 1931, 2324–2328, vol. 53.

Gordon, et al., "Studies on Calcium Levulinate with special Reference to the Influence on Edema", 507–511, The Journal of Laboratory and Clinical Medicine.

Kitano, et al., "Levulinic Acid, A New Chemical Raw Material–Its Chemistry and Use", Jul., 1975, 25–29, Chemical Economy & Engineering Review.

Thomas, et al., "Biomass Derived Levulinic Acid Derivatives and Their Use as Liquid Fuel Extenders", 33–348, Medical Research Institute and Chemical Engineering Program, Florida Inst. of Technology.

Thomas, et al., "Conversion of Cellulose Hydrolysis Products to Fuels and Chemical Feedstocks", 1461–1495, Florida Institue of Technology.

Kuster, "5–Hydroxymethylfurfural (HMF). A Review Foucussing on its Manufacture", 1990, 314–321, Starch/Stärke 42 (1990) Nr. 8.

Velíšek, et al., "Chlorine–containing Compounds Derived from Saccharides in Protein Hydrolysates. II. Levulinic Acid Esters in Soybean Meal Hydrolysates", 1993, 430–433, Levensm.–Wiss. u.–Technol., 26.

Proskouriakoff, "Some Salts of Levulinic Acid", May, 1933, 2132–2134, The Journald of the American Chemical Society, 5.

Wiggins, "Utilization of Sucrose", 1949, 306–314, Advance in Carbohydrate Chemistry, 4.

*Primary Examiner*—Amelia Owens
*Attorney, Agent, or Firm*—Suiter & Associates P.C.

[57] ABSTRACT

The present invention relates to a continuous process for preparing levulinic acid from starch in a reactive extrusion process. In a preferred embodiment, the extrusion takes place in a twin-screw extruder having a plurality of temperature zones wherein the starch slurry is preconditioned, extruded, filter pressed, reboiled, vacuum distilled, condensed, centrifuged, whereby the waste effluent from the centrifugation is reprocessed upstream to the preconditioning stage.

47 Claims, 4 Drawing Sheets

METHOD AND APPARATUS FOR PRODUCTION OF LEVULINIC ACID VIA REACTIVE EXTRUSION

RELATED APPLICATIONS

This application claims priority under 35 U.S.C. § 119(e) based on Provisional Application No. 601018,096, filed May 22, 1996.

TECHNICAL FIELD

The present invention relates generally to methods and apparatus dedicated to the production of levulinic acid and more particularly to an improved method and apparatus for producing levulinic acid via reactive extrusion.

BACKGROUND OF THE INVENTION

Levulinic acid, or 4-oxopentanoic acid, is the simplest member of the comparatively rare class of organic compounds known as gamma-keto acids. Having both a ketonic carbonyl group and an acidic carboxyl group, it reacts as a ketone and as a fatty acid. The chemical structure of levulinic acid may be represented as:

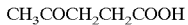

$CH_3COCH_2CH_2COOH$

Levulinic acid is a starting product for the preparation of organic chemicals, dyestuffs, polymers, pharmaceutically active compounds, and flavor substances. Levulinic acid is also an inhibitor of chlorophyll synthesis. Where levulinic acid is utilized in edible compositions rigorous purity, color and stability requirements must be met.

Esters of levulinic acid are known to be useful as plasticizers and solvents, and have been suggested as fuel additives. Levulinic acid is useful as a solvent, food flavoring agent and as a starting material in the preparation of a variety of industrial and pharmaceutical compounds such as diphenolic acid (useful as a component of protective and decorative finishes), calcium levulinate (a particularly suitable form of calcium for intravenous injection used for calcium replenishment and to treat hypocalcemic states, see Cox et al., U.S. Pat. No. 2,033,909).

Levulinic acid is also useful in preparing a glass-like synthetic resin and as a constituent of hydraulic brake fluids and in the manufacture of nylon and rubber. The use of the sodium salt of levulinic acid as a replacement for ethylene glycols as an antifreeze has also been proposed.

DESCRIPTION OF THE PRIOR ART

Levulinic acid has been synthesized by a variety of chemical methods. The preparation of levulinic acid from carbohydrates by the action of mineral acids is known from G. J. Mulder, *J. Prakt. Chem.* 21, 219 (1840), cited in U.S. Pat. No. 5,189,215. Formic acid and other by-products are also formed in this reaction.

Early work on levulinic acid involved reacting different carbohydrate sources with mineral acids. Levulinic acid has been produced by the action of acids on carbohydrates such as glucose (Sah and Ma, 1930); galactose and sucrose (Wiggins, 1949; Thomas and Schuette, 1931); fructose, glucosamine, chitose, sorbose, deoxypentoses, and hexose (Sassenrath and Shilling, 1966; Thompson, 1940); cane sugar and starch (McKenzie, 1929; Moyer, 1942); and disaccharide and polysaccharide unions (Wiggins, 1949). Table 1 (adapted from Thomas and Barile, 1985) summarizes biomass feedstocks for levulinic acids preparation. High yields of levulinic acid were not reported, the authors being primarily concerned with the types of carbohydrates which produced it. Yields were usually less than 25%.

TABLE 1. BIOMASS FEEDSTOCKS OF LEVULINIC ACID PRODUCTION

1. Waste plant material: hard wood or beech bark (Kin et al., 1978)
2. Fiberboard industry waste water (Pajak and Kryczko, 1979)
3. Bagasse pity, bagasse, molasses (Nee and Yse, 1975)
4. Post-fermentation liquor (Mel'nikov et al., 1972)
5. Furfural still residues (Badovskaya et al., 1972)
6. Aqueous oak wood extracts (Prosinski et al., 1971)
7. Rice hull (Sumiki, 1948)
8. Oats residues (Rodriguez, 1973)
9. Wood sugar slops (Faerber, 1943)
10. Fir sawdust (Haworth, 1966)
11. Naphtha (Kikuchi and Ikematsu, 1974)
12. Corncob furfural residue (Dunlop and Wells, 1957)
13. Cotton balls, rice, straw, soybean skin, soybean oil residue, corn husks (Sumiki and Kojima, 1944)
14. Cotton stems (Minina et al., 1962)
15. Cottonseed hulls (Akmamedov, 1962)
16. Molasses (Rao et al., 1959)
17. Starch (Hands and Whitt, 1947)
18. Potatoes, sweet potatoes, lactose (Takahashi, 1944)
19. Waste wood pulping residues (Wiley et al., 1955)
20. Sunflower seed husks (Shil'nikova, 1967)
21. Tapioca meal (Chapman, 1971)

The studies done varying the method of preparation of levulinic acid were beneficial, since such studies have led to the improvement of process efficiency. Thompson (1940) found that addition of NaCl to a solution of HCl and sucrose or other carbohydrate increased the yield. Thomas and Schuette (1931) showed that if sucrose was digested under pressure with dilute HCl at 162° C. for one hour, a 42% yield of levulinic acid was obtained. Wiggins (1949) indicated that the concentration of sucrose was a critical factor and that the highest yields were obtained with very dilute solutions. Furthermore, he found that by carrying out the reaction between sucrose and minerals acids the efficacy of the different acids was as follows $HBr > HCl > H_2SO_4$. Thomas and Barlie (1985) reported better yields with $H_2SO_4$ than with HCl. The highest yield of levulinic acid, weighted as crude material, was 79% of the theoretical and was obtained when the concentration of sucrose was 3%. Ploetz (1943) also used the HBr acid method to make levulinic acid and recorded a yield of 69% of the theoretical from can sugar, 75% from glucose, and 64% from starch. McKibbins (1962) used an autoclave to increase reaction temperatures to 160°–200° C. and thereby increase yields. The effects of acid concentrations and type also were studied.

Commercial production using an autoclave began in the United States in 1940 by A. E. Staley Co. using starch as the feed and HCl (Moyer, 1942). The isolation of levulinic acid was accomplished by partial neutralization, filtration of humin materials and vacuum steam distillation (FIG. 4) (Moyer, 1942). Four additional patents exist (Redmon, 1956; Dunlop and Wells, 1957; Carlson and Wash, 1962; Sassenrath and Shilling, 1966). The Redmon process employs an ion exchange catalyst. The advantages of an ion exchange process are: (1) little humin (solid waste) byproduct, (2) low reaction temperature, and (3) the catalyst can be separated readily from the reaction mixture and regenerated. The patent to Dunlop and Wells (1957) describes an atmospheric pressure process for producing levulinic acid from hexose-yielding substance ranging from sucrose to cellulosic wastes such as corn cobs, bagasse, grain hulls, and wood products. The patent to Carlson and Wash (1962) refers to an improved cyclic process of manufacture wherein a carbohydrate such as cellulose is hydrolyzed with a dilute mineral acid at an elevated temperature and then converted to levulinic acid. A flow sheet of the process is shown FIG. 2. Sassenrath and Shilling's (1966) patent refers to an economically feasible commercial process for producing levulinic acid. The yield of levulinic acid was increased, as compared to the previous process, by recycling of the lactones and wash liquor which retarded the yield. The flow sheet of the process is shown FIG. 3.

Herndon (1950) prepared an engineering study on the production of levulinic acid from sucrose. Even though the cost data are more than 45 years old, areas that must be considered to improve the economic picture are well documented. Cheap feedstocks are needed, such as pulp or crop wastes. The reaction conditions must be such that high yields are produced with a minimum amount of heat input. More efficient ways should be found to extract and purify the acid. The acid catalyst should be easily separated from the solution. For the latter reason, an effort was made by Schraufnagel and Rase (1975) to produce levulinic acid and 5-HMF using ion exchange resins as catalysts and sucrose as a convenient soluble polysaccharide. Ion exchange resins are attractive for this process because of the selectivity possible by pore size control and the reusable character of a solid catalyst. Although it is possible to produce levulinic acid at moderate temperatures (100° C.) using ion exchange resins in the acid form, the rates are very low.

DEA 2,112,726 discloses a preparation of levulinic acid from furfuryl alcohol via ring cleavage with hydrochloric or oxalic acid. However, to improve the yield, this process is carried out in a very dilute solution and is disadvantageous in that entails a high energy consumption in separating off the solvent.

More recent prior art teachings disclose various other methods of producing levulinic acid. For example, Farnleitner et al. disclose a process for preparing storage-stable levulinic acid by treating a mixture of acetylsuccinate and aqueous mineral acid with steam.

Likewise, levulinic acid may be produced by boiling hexoses, or other carbohydrates containing hexoses, with dilute mineral acid for approximately 20 hours and then separating by vacuum distillation.

Fitzpatrick et al. (U.S. Pat. No. 4,897,947) disclose a method of degrading lignocellulose to furfural and levulinic acid. Hsu et al. (U.S. Pat. No. 4,236,021) disclose a method of preparing levulinic acid from furfuryl alcohol. Ueno et al. (U.S. Pat. No. 3,663,368) disclose a method of removing levulinic acid with microorganisms.

SUMMARY OF THE INVENTION

The present invention provides an improved method and apparatus for producing levulinic acid with bifunctional chemical intermediates made by hydrolyzing starch and dilute acid in an extruder.

Extrusion is generally a processing operation wherein a material is forced through a metal die. With high viscosity materials, a rotating screw of variable pitch is used to force the material through the die. Items extruded are, for example, injection molding polymers, molten glass, hot metal billet, and food items, such as spaghetti and the like.

It has unexpectedly been found that, in accordance with the present invention, extrusion processing of a starch acid slurry provides a very efficient method for the production of levulinic acid. Extrusion production, as herein described, is advantageous in that the process is continuous, requires fewer steps and reduced reaction times, and gives higher yields at a reduced cost. The present invention, in a preferred embodiment, prepares levulinic acid from starch via a twin-screw extruder having a plurality of temperature zones wherein the starch slurry is preconditioned, extruded, filter pressed, reboiled, vacuum distilled, condensed, centrifuged, and reprocessed.

Additionally, the present invention may be utilized to prepare valeric γ-lactone by hydrogenation of levulinic acid. Valeric γ-lactone is an excellent solvent.

Further, the present invention may be utilized to prepare 1,4-pentanediol, which on dehydration yields 1,3-pentadiene (piperylene). Piperylene is known to polymerize to an elastomer.

Despite the wide utility possessed by levulinic acid as described above, it is felt that its commercial potential is impeded by the high production costs and low yields of the currently available processes. It is therefore an object of the present invention to provide a process and apparatus for the production of levulinic acid at a cost lower than the current commercial processes.

To date, the preparation of levulinic acid from starch has been confined to batch processes. The commercial processes that operate continuously have used cellulose starting materials. It is therefore another object of the present invention to provide a continuous process and apparatus for the preparation of levulinic acid wherein starch is employed as the starting material.

It is another object of the present invention to provide a process and apparatus for the preparation of levulinic acid which requires milder reaction conditions, shorter reaction times, and fewer steps than the prior art processes.

It is a further object of the invention to provide a process and apparatus for the preparation of levulinic acid that gives increased yields over the prior art processes. The process of the present invention gives yields of about 48% which is about 70% of theoretical.

It is yet another object of the invention to provide a process and apparatus for the preparation of levulinic acid whereby the some or all of the waste stream is recycled to the beginning of the process.

Still further objects and advantages will become apparent from a consideration of the ensuing description and drawings.

BRIEF DESCRIPTION OF THE DRAWINGS

The numerous objects and advantages of the present invention may be better understood by those skilled in the art by reference to the accompanying figures in which.

DETAILED DESCRIPTION OF THE INVENTION

Figure 1:
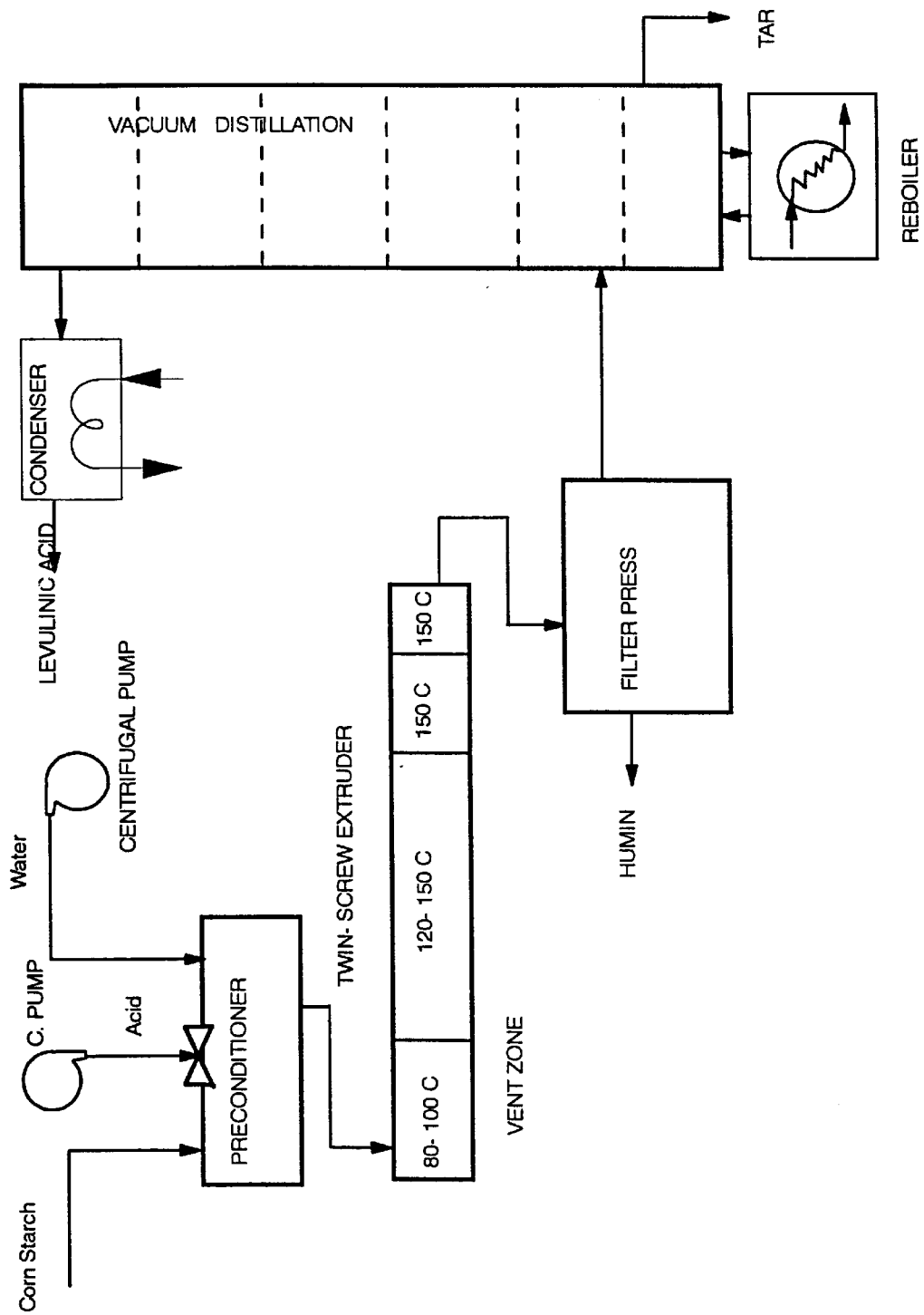
FIG. 1 is diagram illustrating the preparation of levulinic acid according to a preferred embodiment of the present invention.
Figure 2:
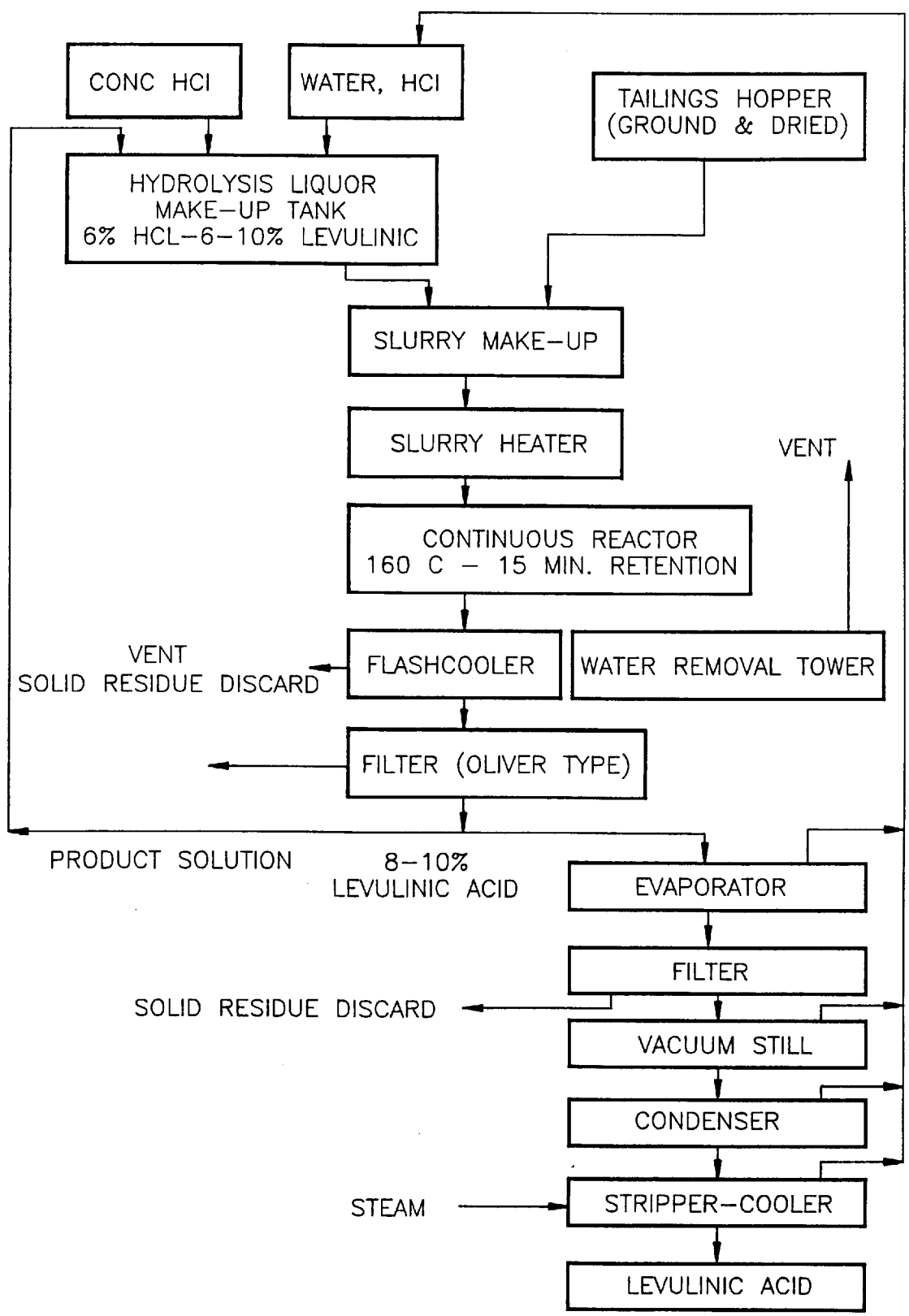
FIG. 2 is a diagram illustrating a prior art method of preparing levulinic acid via a reactor and evaporator.
Figure 3:
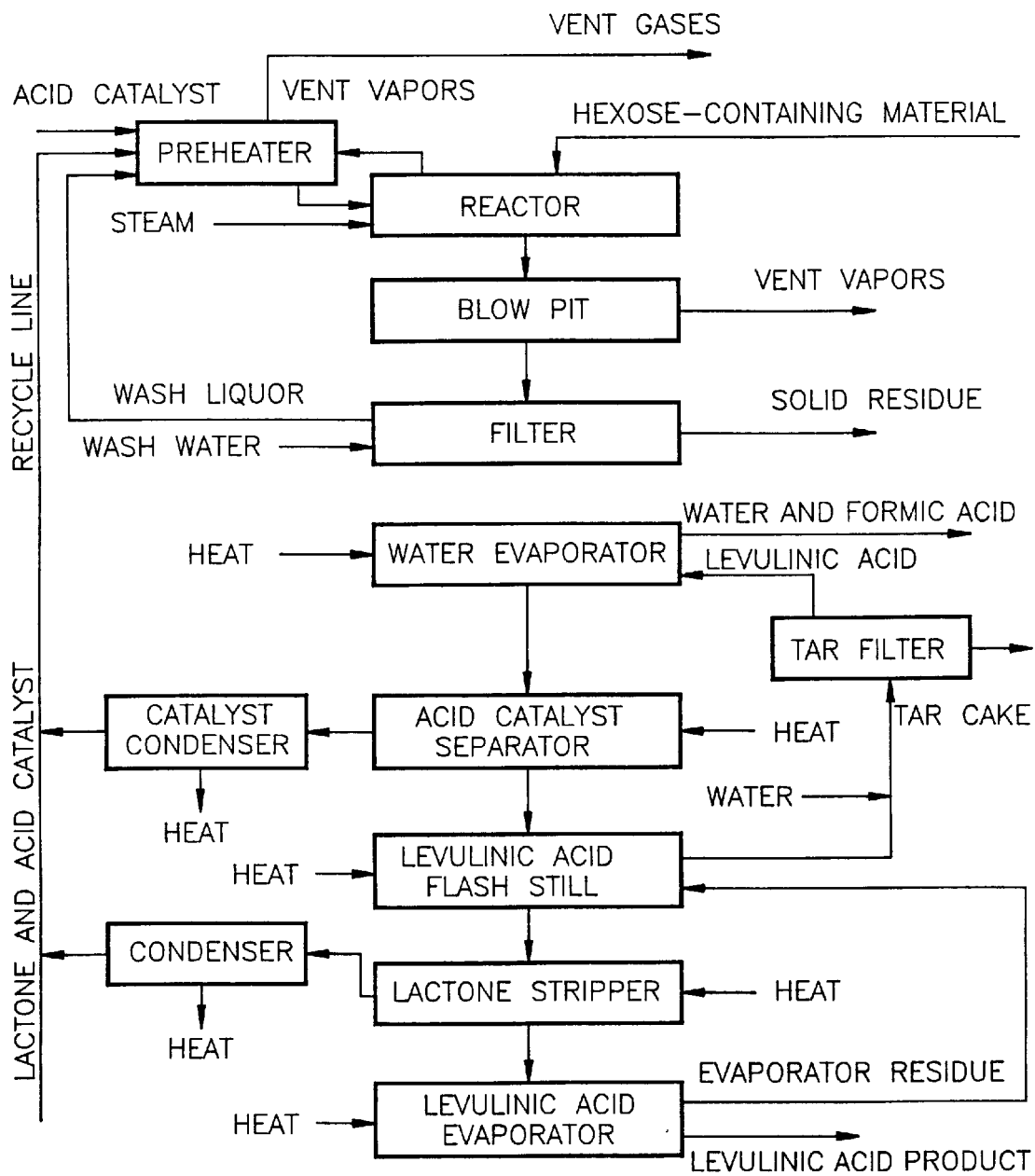
FIG. 3 is a diagram illustrating yet another prior art method of preparing levulinic acid via a reactor, blow pit, filter, and evaporator system.
Figure 4:
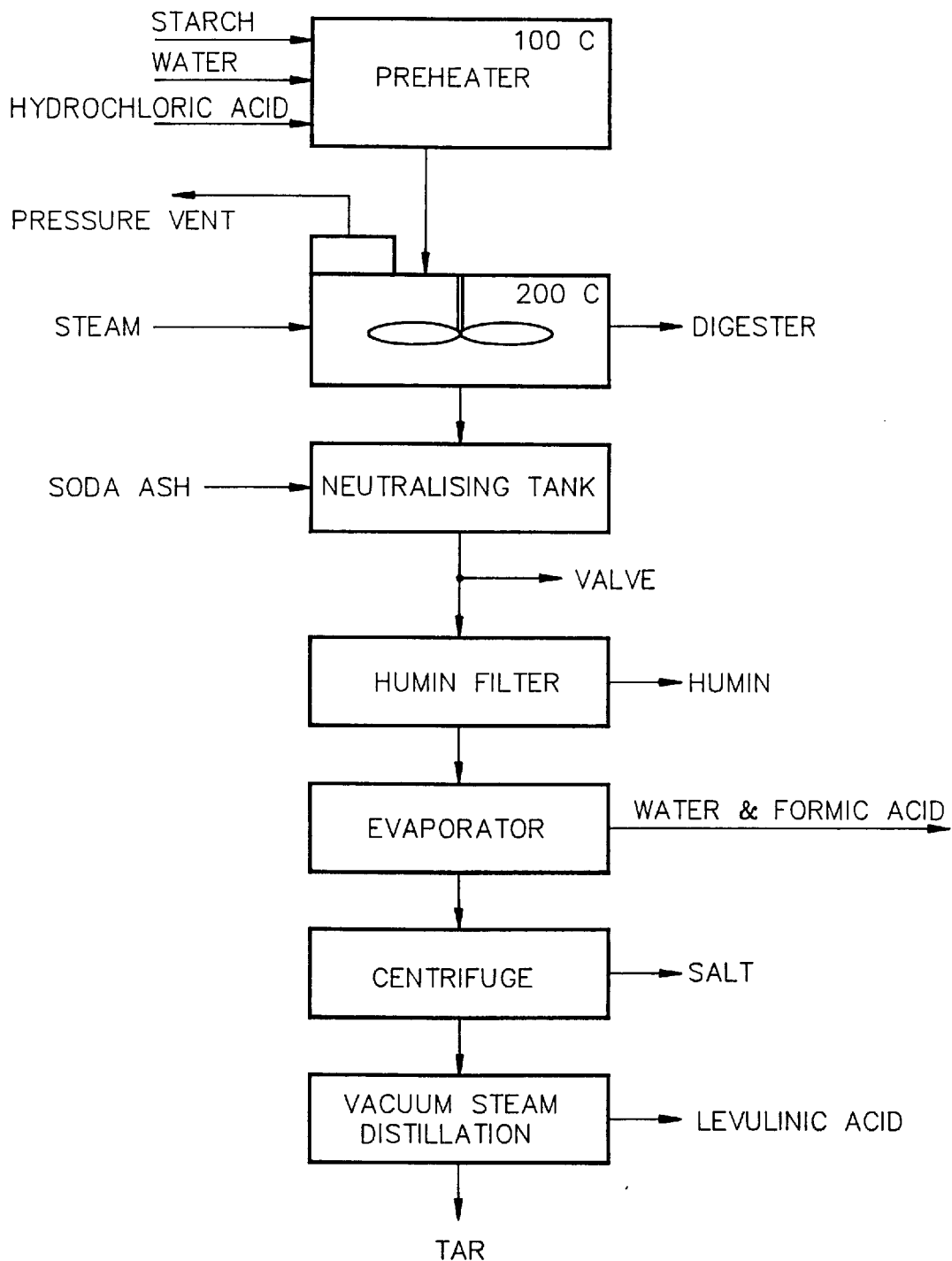
FIG. 4 is a diagram illustrating still another prior art method of preparing levulinic acid via a steam digester.

A typical embodiment of the process of the present invention is illustrated in FIG. 1. Corn starch, water, and acid are fed to a preconditioner. The slurry thus formed is then fed to the twin-screw extruder. After extrusion, the extrudate is filtered and the levulinic acid is separated from the filter press discharge product by vacuum distillation.

Starch from any source may be used in the present invention. Especially preferred is starch containing approximately 20–70% amylose, with 25% being most preferred. Wheat, corn, rice, and tapioca starch are of particular interest in the present invention, with corn starch being especially preferred.

Any strong mineral acid can be employed in the present invention. Preferred are HBr, HCl, and $H_2SO_4$, with $H_2SO_4$ being the most preferred.

In a particularly preferred embodiment of the present invention, the starch, acid, and water, are combined to form a slurry in a preconditioning step. The preconditioning step ensures a good mix of the starch, acid, and water.

The preferred ratios of starch, water, and acid are about 54–67 parts starch, 30–40 parts water, and 3 to 6 parts acid. The pH of the resulting slurry is preferably less than 1. The slurry remains in the preconditioning stage for 3 to 4 hours.

The extruders useful herein can vary. Although single screw extruders may be used, it is preferred to use twin-screw extruders. Of particular interest are extruders which also provide for heating of the materials introduced into the extruder.

In a particularly preferred embodiment of the invention, a C. W. Brabender twin-screw extruder (model D-6) is used. The screw used is a counter-rotating conical twin-screw (mixing type) having a decreasing diameter fro 43 mm to 28 mm along its length of 370 mm. A 3 mm long die having a 15 mm orifice opening is preferably used with a 9 mm nozzle attached to the die end of the extruder.

Other suitable extruders include, but are not limited to, the Wenger TX-115 twin screw extruder, Wenger X-165 single screw extruder, and the like.

In another preferred embodiment of the present invention, the extruder is equipped with a degassing port for venting gasses during the extrusion process.

In a preferred embodiment of the present invention, the extrusion takes place at an elevated temperature. The temperature in the extruder is preferably from about 120° C. to about 160° C., with 150° C. at the die being especially preferred. In particularly preferred embodiment, an extruder with a plurality of temperature zones is employed. Preferably, a variable temperature profile of 80°–100° C./120°–150° C./150° C. is employed, as shown in FIG. 1, with 100° C./150° C./150° C. being the most preferred.

In another preferred embodiment of the present invention, the slurry passes through the extruder at a flow rate of approximately 80 ml/minute, or, alternatively, has a residence time of from about 80 to about 100 seconds.

After the extrudate exits the extruder die, the levulinic acid can be separated from the extrudate by any means known to those skilled in the art. The preferred means of separating levulinic acid are partial neutralization, filtration/vacuum steam distillation, and solvent extraction. In a preferred embodiment, the extrudate is filter pressed and the resulting filtrate is subjected to steam distillation. In an especially preferred embodiment, the discharge product of the distillation containing the levulinic acid is condensed and centrifuged and some or all of the liquor discharged from the centrifugation is recycled to the preconditioning step.

The vacuum distillation of crude levulinic acid has long been known to those skilled in the art. See, for example, Hands et al., *J.S.C.I.*, 66, 415–16 (1947), herein incorporated by reference in its entirety.

The following example serves to illustrate the invention.

EXAMPLE

Amaizo 100 industrial grade corn starch (25% Amylose), 5% sulfuric acid and water are fed to the preconditioning unit at a rates of 1800 lb/hour, 22.15 liters/h (92.10 lb/hour), and 650 lb/hour, respectively. The temperature of the dry materials is 25° C. The processing water temperature is 60° C. The preconditioner discharge temperature is 100° C. The preconditioner discharge moisture is 40% (wet basis). The extruder temperature profile is 100°-150°-150° C. The die temperature is 140° C. The extrudate is pressed in a US Filters FP-100 filter press and the filtrate is subjected to vacuum distillation in a Chemtowers VDC-125. The discharge from the vacuum distillation is condensed and centrifuged.

The description above should not be construed as limiting the scope of the invention, but as merely providing illustrations to some of the presently preferred embodiments of this invention. In light of the above description and examples, various other modifications and variations will now become apparent to those skilled in the art without departing from the spirit and scope of the present invention as defined by the appended claims. Accordingly, the scope of the invention should be determined solely by the appended claims and their legal equivalents.

All references cited herein are hereby expressly incorporated by reference in their entireties.

What is claimed is:

1. A process for preparing levulinic acid from starch, comprising the steps of mixing starch, water, and a mineral acid so as to form a slurry; extruding said slurry with an extruder to form an extrudate containing levulinic acid.

2. The process according to claim 1 wherein said starch has an amylose content of from about 20% to about 30%.

3. The process according to claim 1 wherein said starch is selected from the group consisting of corn starch, wheat starch, rice starch, tapioca starch, and mixtures thereof.

4. The process according to claim 1 wherein said mineral acid is selected from the group consisting of hydrochloric acid, hydrobromic acid, and sulfuric acid.

5. The process according to claim 1 wherein said mineral acid is sulfuric acid and wherein said starch is corn starch.

6. The process according to claim 1 wherein said extruder is a twin-screw extruder.

7. The process according to claim 1 further comprising the step of heating said slurry in the extruder to temperatures ranging between about 80° C. and about 150° C.

8. The process according to claim 1 further comprising the step of mixing and heating said slurry to precondition the slurry before it is fed to the extruder.

9. The process according to claim 1, comprising the steps of mixing starch, water, and a mineral acid so as to form a slurry; extruding said slurry with an extruder to form an extrudate containing levulinic acid; and separating levulinic acid from the extrudate.

10. The process according to claim 9 wherein said starch has an amylose content of from about 20–30%.

11. The process according to claim 10 wherein said starch has an amylose content of about 25%.

12. The process according to claim 9 wherein said starch is selected from the group consisting of corn starch, wheat starch, rice starch, tapioca starch, and mixtures thereof.

13. The process according to claim 12 wherein said starch is corn starch.

14. The process according to claim 9 wherein said mineral acid is selected from the group consisting of hydrochloric acid, hydrobromic acid, and sulfuric acid.

15. The process according to claim 14 wherein said mineral acid is sulfuric acid.

16. The process according to claim 9 further comprising the step of heating said slurry in the extruder to temperatures ranging between about 80° C. and about 150° C.

17. The process according to claim 16 wherein said extruder is a twin-screw extruder.

18. The process according to claim 17 wherein the barrel of the extruder has a plurality of temperature zones having different temperatures.

19. The process according to claim 9 wherein said extruder is a twin-screw extruder.

20. The process according to claim 9 further comprising the step of mixing and heating said slurry to precondition the slurry before it is fed to the extruder.

21. The process according to claim 9 wherein gases are vented from said extruder during the extrusion step.

22. The process according to claim 9 wherein separating levulinic acid from the extrudate comprises one or more steps selected from the group consisting of partial neutralization, filtration, and solvent extraction of the extrudate.

23. The process according to claim 22 comprising the step of separating levulinic acid from the extrudate by filtering the extrudate to produce a filtrate, and further comprising the step of distilling said filtrate.

24. The process according to claim 23 wherein said distillation step is performed under a vacuum.

25. The process according to claim 24 wherein said distillation step is performed in the presence of steam.

26. The process according to claim 9 wherein the step of separating levulinic acid from the extrudate comprises filter pressing the discharge product of the extruder and vacuum distilling the discharge product of the filter press.

27. The process according to claim 26 wherein the step of separating levulinic acid from the extrudate comprises filter pressing the discharge product of the extruder, vacuum distilling the discharge product of the filter press, condensing the discharge product of the vacuum distiller so as to produce a mixture containing levulinic acid, and centrifuging said mixture containing levulinic acid.

28. The process according to claim 27 wherein at least a portion of the liquor discharged from said centrifuge is recycled by mixing with said water to be mixed with said starch and mineral acid to be utilized in continuation of said process.

29. The process according to claim 26 wherein said starch has an amylose content of from about 20–30%.

30. The process according to claim 26 wherein said starch has an amylose content of from about 23–25%.

31. The process according to claim 26 wherein said starch is selected from the group consisting of corn starch, wheat starch, rice starch, tapioca starch, and mixtures thereof.

32. The process according to claim 31 wherein said starch is corn starch.

33. The process according to claim 26 wherein said mineral acid is selected from the group consisting of hydrochloric acid, hydrobromic acid, and sulfuric acid.

34. The process according to claim 33 wherein said mineral acid is sulfuric acid.

35. The process according to claim 26 wherein said extruder is a twin-screw extruder.

36. The process according to claim 35 further comprising the step of heating said slurry in the extruder to temperatures ranging between about 80° C. and about 150° C.

37. The process according to claim 36 wherein the barrel of the extruder has a plurality of temperature zones.

38. The process according to claim 27 further comprising the step of mixing and heating said slurry to precondition the slurry before it is fed to the extruder.

39. The process according to claim 27 wherein gases are vented from said extruder.

40. The process according to claim 27 wherein humin is a byproduct of the filter press.

41. The process according to claim 27 wherein a reboiler is utilized to reheat the discharge material from said filter press during the vacuum distillation step.

42. The process according to claim 27 wherein tar is discharged as a reaction byproduct during said vacuum distillation.

43. The process according to claim 1, comprising the steps of:

mixing starch, water, and a mineral acid so as to form a slurry;

extruding said slurry in an extruder at a temperature of from about 80° C. to about 150° C.;

filter pressing the discharge product of the extruder vacuum distilling the discharge product of the filter press;

condensing the discharge product of the vacuum distiller so as to produce a mixture containing levulinic acid; and centrifuging said mixture containing levulinic acid;

wherein said starch is selected from the group consisting of corn starch, wheat starch, rice starch, tapioca starch, and mixtures thereof; wherein said slurry is preconditioned by heating and mixing prior to extruding said slurry; wherein at least a portion of the liquor discharged from said centrifuge is recycled by mixing with said water to be mixed with said starch and mineral acid to be utilized in continuation of said process.

44. Levulinic acid prepared by the process of claim 1.

45. A process for preparing valeric γ-lactone comprising the steps of mixing starch, water, and a mineral acid so as to form a slurry; extruding said slurry with an extruder to form an extrudate containing levulinic acid; separating levulinic acid from the extrudate; and hydrogenating said levulinic acid to obtain valeric γ-lactone.

46. A process for preparing 1,3-pentadiene comprising the steps of mixing starch, water, and a mineral acid so as to form a slurry; extruding said slurry with an extruder to form an extrudate containing levulinic acid; separating levulinic acid from the extrudate; reducing the ketone and carboxy moieties of said levulinic acid to obtain 1,4-pentandiol; and dehydrating said 1,4-pentandiol to yield 1,3-pentadiene.

47. A process for preparing 1,4-pentanediol comprising the steps of mixing starch, water, and a mineral acid so as to form a slurry; extruding said slurry with an extruder to form an extrudate containing levulinic acid; separating levulinic acid from the extrudate; and reducing the ketone and carboxy moieties of said levulinic acid to obtain 1,4-pentandiol.

* * * * *